(12) United States Patent
Sampson et al.

(10) Patent No.: US 7,731,712 B2
(45) Date of Patent: Jun. 8, 2010

(54) METHOD AND SYSTEM FOR TRANSCERVICAL TUBAL OCCLUSION

(75) Inventors: Russel M. Sampson, Palo Alto, CA (US); Eugene V. Skalnyi, Los Altos, CA (US); Estela H. Hilario, Los Altos, CA (US); J. Brook Burley, Sunnyvale, CA (US)

(73) Assignee: CYTYC Corporation, Marlborough, MA (US)

( * ) Notice: Subject to any disclaimer, the term of this patent is extended or adjusted under 35 U.S.C. 154(b) by 1504 days.

(21) Appl. No.: 11/019,580

(22) Filed: Dec. 20, 2004

(65) Prior Publication Data

US 2006/0135956 A1 Jun. 22, 2006

(51) Int. Cl.
*A61B 18/18* (2006.01)
(52) U.S. Cl. .......................................... 606/41; 606/50
(58) Field of Classification Search .................. 606/41, 606/45–50; 607/101–105, 116, 138
See application file for complete search history.

(56) References Cited

U.S. PATENT DOCUMENTS

| | | | |
|---|---|---|---|
| 552,832 | A | 1/1896 | Fort |
| 725,731 | A | 4/1903 | Linn |
| 1,620,929 | A | 3/1927 | Wallerich |
| 1,827,306 | A | 10/1931 | Chapman et al. |
| 2,190,383 | A | 2/1940 | Newman |
| 2,347,195 | A | 4/1944 | Huff |
| 2,466,042 | A | 4/1949 | Reich et al. |
| 3,228,398 | A | 1/1966 | Leonard et al. |
| 3,324,855 | A | 6/1967 | Heimlich |
| 3,645,265 | A | 2/1972 | Majzlin |
| 3,840,016 | A | 10/1974 | Lindemann |
| 3,845,771 | A | 11/1974 | Vise |

(Continued)

FOREIGN PATENT DOCUMENTS

DE 384246 10/1923

(Continued)

OTHER PUBLICATIONS

D.E. Haines et al., "Observations on Electrode-Tissue Interface Temperature and Effect on Electrical Impedance During Radiofrequency Ablation of Ventricular Myocardium," *Circulation*, vol. 82, No. 3, Sep. 1990, pp. 1034-1038.

(Continued)

*Primary Examiner*—Michael Peffley
(74) *Attorney, Agent, or Firm*—Marc A. Vivenzio

(57) ABSTRACT

A medical device and procedure is described for occluding a fallopian tube. A tubal occlusion device is inserted into a uterine cavity. The device includes an RF applicator head including an electrode carrier with one or more bipolar electrodes thereon. During insertion, the RF applicator head can be in a closed position. The RF applicator head is positioned at a tubal ostium of a fallopian tube, such that a distal tip of the RF applicator head advances into the tubal ostium. The RF applicator head is deployed into an open position such that the RF applicator head approximates the shape of the uterine cavity in a region of the tubal ostium. Current is passed through the one or more bipolar electrodes to the tubal ostium to destroy tissue to a known depth, which precipitates a healing response in surrounding tissue that over time scars and occludes the fallopian tube.

8 Claims, 8 Drawing Sheets

U.S. PATENT DOCUMENTS

| | | |
|---|---|---|
| 3,858,586 A | 1/1975 | Lessen |
| 3,877,464 A | 4/1975 | Vermes |
| 3,924,628 A | 12/1975 | Droegemueller et al. |
| 3,948,270 A | 4/1976 | Hasson |
| 3,967,625 A | 7/1976 | Yoon |
| 3,971,378 A | 7/1976 | Krantz |
| 4,022,215 A | 5/1977 | Benson |
| 4,057,063 A | 11/1977 | Gieles et al. |
| 4,082,096 A | 4/1978 | Benson |
| 4,158,050 A | 6/1979 | Zipper |
| 4,185,618 A | 1/1980 | Corey |
| 4,233,025 A | 11/1980 | Larson et al. |
| 4,359,454 A | 11/1982 | Hoffman |
| 4,380,238 A | 4/1983 | Colucci et al. |
| 4,415,288 A | 11/1983 | Gordon et al. |
| 4,449,528 A | 5/1984 | Auth et al. |
| 4,465,072 A | 8/1984 | Taheri |
| 4,492,231 A | 1/1985 | Auth |
| 4,532,924 A | 8/1985 | Auth et al. |
| 4,568,326 A | 2/1986 | Rangaswamy |
| 4,582,057 A | 4/1986 | Auth et al. |
| 4,601,698 A | 7/1986 | Moulding, Jr. |
| 4,606,336 A | 8/1986 | Zeluff |
| 4,628,924 A | 12/1986 | Cimber |
| 4,662,383 A | 5/1987 | Sogawa et al. |
| 4,676,258 A | 6/1987 | Inokuchi et al. |
| 4,682,809 A * | 7/1987 | Huss ..................... 296/181.2 |
| 4,691,703 A | 9/1987 | Auth et al. |
| 4,765,331 A | 8/1988 | Petruzzi et al. |
| 4,788,966 A | 12/1988 | Yoon |
| 4,832,048 A | 5/1989 | Cohen |
| 4,865,047 A | 9/1989 | Chou et al. |
| 4,869,268 A | 9/1989 | Yoon |
| 4,946,440 A | 8/1990 | Hall |
| 4,949,718 A | 8/1990 | Neuwirth et al. |
| 4,955,377 A | 9/1990 | Lennox et al. |
| 4,960,133 A | 10/1990 | Hewson |
| 4,961,435 A | 10/1990 | Kitagawa et al. |
| 4,979,948 A | 12/1990 | Geddes et al. |
| 4,981,465 A | 1/1991 | Ballan et al. |
| 4,983,177 A | 1/1991 | Wolf |
| 5,026,379 A | 6/1991 | Yoon |
| 5,047,028 A | 9/1991 | Qian |
| 5,057,106 A | 10/1991 | Kasevich et al. |
| 5,065,751 A | 11/1991 | Wolf |
| 5,078,717 A | 1/1992 | Parins et al. |
| 5,084,044 A | 1/1992 | Quint |
| 5,105,808 A | 4/1992 | Neuwirth et al. |
| 5,147,353 A | 9/1992 | Everett |
| 5,159,925 A | 11/1992 | Neuwirth et al. |
| 5,186,181 A | 2/1993 | Franconi et al. |
| 5,188,122 A | 2/1993 | Phipps et al. |
| 5,188,602 A | 2/1993 | Nichols |
| 5,217,473 A | 6/1993 | Yoon |
| 5,226,908 A | 7/1993 | Yoon |
| 5,242,437 A | 9/1993 | Everett et al. |
| 5,248,312 A | 9/1993 | Langberg |
| 5,263,585 A | 11/1993 | Lawhon et al. |
| 5,277,201 A | 1/1994 | Stern |
| 5,308,327 A | 5/1994 | Heaven et al. |
| 5,318,532 A | 6/1994 | Frassica |
| 5,322,507 A | 6/1994 | Costello et al. |
| 5,334,193 A | 8/1994 | Nardella |
| 5,334,209 A | 8/1994 | Yoon |
| 5,354,295 A | 10/1994 | Guglielmi et al. |
| 5,364,393 A | 11/1994 | Auth et al. |
| 5,370,649 A | 12/1994 | Gardetto et al. |
| 5,374,261 A | 12/1994 | Yoon |
| 5,374,283 A | 12/1994 | Flick |
| 5,380,317 A | 1/1995 | Everett et al. |
| 5,383,917 A | 1/1995 | Desai et al. |
| 5,395,311 A | 3/1995 | Andrews |
| 5,405,322 A | 4/1995 | Lennox et al. |
| 5,407,071 A | 4/1995 | Lawhon et al. |
| 5,433,708 A | 7/1995 | Nichols et al. |
| 5,437,629 A | 8/1995 | Goldrath |
| 5,443,470 A | 8/1995 | Stern et al. |
| 5,451,204 A | 9/1995 | Yoon |
| 5,474,089 A | 12/1995 | Waynant |
| 5,505,730 A | 4/1996 | Edwards |
| 5,507,743 A | 4/1996 | Edwards et al. |
| 5,507,744 A * | 4/1996 | Tay et al. ..................... 606/50 |
| 5,514,091 A | 5/1996 | Yoon |
| 5,562,703 A | 10/1996 | Desai |
| 5,562,720 A | 10/1996 | Stern et al. |
| 5,588,961 A | 12/1996 | Leone et al. |
| 5,593,404 A | 1/1997 | Costello et al. |
| 5,609,598 A | 3/1997 | Laufer et al. |
| 5,613,950 A | 3/1997 | Yoon |
| 5,626,576 A * | 5/1997 | Janssen ..................... 606/41 |
| 5,649,924 A | 7/1997 | Everett et al. |
| 5,656,013 A | 8/1997 | Yoon |
| 5,667,520 A | 9/1997 | Bonutti |
| 5,697,882 A | 12/1997 | Eggers et al. |
| 5,702,438 A | 12/1997 | Avitall |
| 5,709,224 A * | 1/1998 | Behl et al. ................. 128/898 |
| 5,716,343 A | 2/1998 | Kriesel et al. |
| 5,730,136 A | 3/1998 | Laufer et al. |
| 5,730,725 A | 3/1998 | Yoon |
| 5,769,880 A | 6/1998 | Truckai et al. |
| 5,779,698 A | 7/1998 | Clayman et al. |
| 5,797,903 A | 8/1998 | Swanson et al. |
| 5,800,482 A | 9/1998 | Pomeranz et al. |
| 5,807,389 A | 9/1998 | Gardetto et al. |
| 5,810,847 A | 9/1998 | Laufer et al. |
| 5,827,273 A | 10/1998 | Edwards |
| 5,843,121 A | 12/1998 | Yoon |
| 5,846,238 A | 12/1998 | Jackson et al. |
| 5,871,469 A | 2/1999 | Eggers et al. |
| 5,879,348 A | 3/1999 | Owens et al. |
| 5,885,601 A | 3/1999 | Sokal |
| 5,888,198 A | 3/1999 | Eggers et al. |
| 5,891,134 A | 4/1999 | Goble et al. |
| 5,891,136 A | 4/1999 | McGee et al. |
| 5,897,551 A | 4/1999 | Everett et al. |
| 5,897,553 A | 4/1999 | Mulier et al. |
| 5,935,137 A | 8/1999 | Saadat et al. |
| 5,938,660 A | 8/1999 | Swartz et al. |
| 5,954,715 A * | 9/1999 | Harrington et al. ............ 606/28 |
| 5,954,717 A | 9/1999 | Behl et al. |
| 6,002,968 A | 12/1999 | Edwards |
| 6,014,589 A | 1/2000 | Farley et al. |
| 6,033,397 A | 3/2000 | Laufer et al. |
| 6,036,687 A | 3/2000 | Laufer et al. |
| 6,041,260 A | 3/2000 | Stern et al. |
| 6,042,596 A | 3/2000 | Bonutti |
| 6,068,613 A | 5/2000 | Kriesel et al. |
| 6,068,626 A | 5/2000 | Harrington et al. |
| 6,071,277 A | 6/2000 | Farley et al. |
| 6,077,257 A | 6/2000 | Edwards et al. |
| 6,096,052 A | 8/2000 | Callister et al. |
| 6,117,101 A | 9/2000 | Diederich et al. |
| 6,123,702 A | 9/2000 | Swanson et al. |
| 6,135,997 A | 10/2000 | Laufer et al. |
| 6,139,527 A | 10/2000 | Laufer et al. |
| 6,152,899 A | 11/2000 | Farley et al. |
| 6,159,207 A | 12/2000 | Yoon |
| 6,164,280 A | 12/2000 | Everett et al. |
| 6,165,172 A | 12/2000 | Farley et al. |
| 6,179,832 B1 | 1/2001 | Jones et al. |
| 6,183,468 B1 | 2/2001 | Swanson |
| 6,200,312 B1 | 3/2001 | Zikorus et al. |
| 6,231,496 B1 | 5/2001 | Wilk et al. |
| 6,231,507 B1 | 5/2001 | Zikorus et al. |

| | | | |
|---|---|---|---|
| 6,234,178 B1 | 5/2001 | Goble | |
| 6,237,606 B1 | 5/2001 | Zikorus et al. | |
| 6,238,393 B1 | 5/2001 | Mulier et al. | |
| 6,245,065 B1 | 6/2001 | Panescu et al. | |
| 6,245,090 B1 | 6/2001 | Gilson et al. | |
| 6,254,601 B1 | 7/2001 | Burbank et al. | |
| 6,258,084 B1 | 7/2001 | Goldman et al. | |
| 6,263,248 B1 | 7/2001 | Farley et al. | |
| 6,277,089 B1 | 8/2001 | Yoon | |
| 6,293,942 B1 | 9/2001 | Goble et al. | |
| 6,296,639 B1 | 10/2001 | Truckai et al. | |
| 6,309,384 B1 | 10/2001 | Harrington et al. | |
| 6,315,776 B1 | 11/2001 | Edwards et al. | |
| 6,322,559 B1 | 11/2001 | Daulton et al. | |
| 6,325,798 B1 * | 12/2001 | Edwards et al. | 606/41 |
| 6,346,102 B1 | 2/2002 | Harrington et al. | |
| 6,352,549 B1 | 3/2002 | Everett | |
| 6,364,877 B1 | 4/2002 | Goble et al. | |
| 6,369,465 B1 | 4/2002 | Swanson | |
| 6,395,012 B1 | 5/2002 | Yoon et al. | |
| 6,398,780 B1 | 6/2002 | Farley et al. | |
| 6,428,537 B1 | 8/2002 | Swanson | |
| 6,432,116 B1 | 8/2002 | Callister et al. | |
| 6,475,213 B1 | 11/2002 | Whayne et al. | |
| 6,485,500 B1 | 11/2002 | Kokish et al. | |
| 6,508,815 B1 | 1/2003 | Strul et al. | |
| 6,554,780 B1 * | 4/2003 | Sampson et al. | 600/587 |
| 6,587,731 B1 * | 7/2003 | Ingle et al. | 607/101 |
| 6,663,626 B2 | 12/2003 | Truckai et al. | |
| 6,679,269 B2 | 1/2004 | Swanson | |
| 6,712,810 B2 | 3/2004 | Harrington et al. | |
| 6,712,815 B2 | 3/2004 | Sampson et al. | |
| 6,726,682 B2 | 4/2004 | Harrington et al. | |
| 6,743,184 B2 | 6/2004 | Sampson et al. | |
| 6,752,803 B2 * | 6/2004 | Goldman et al. | 606/32 |
| 6,764,488 B1 | 7/2004 | Burbank et al. | |
| 6,813,520 B2 | 11/2004 | Truckai et al. | |
| 6,939,348 B2 * | 9/2005 | Malecki et al. | 606/41 |
| 2001/0041900 A1 | 11/2001 | Callister et al. | |
| 2002/0022870 A1 * | 2/2002 | Truckai et al. | 607/101 |
| 2002/0029051 A1 | 3/2002 | Callister et al. | |
| 2002/0072499 A1 | 6/2002 | Clagett | |
| 2002/0072745 A1 | 6/2002 | Truckai et al. | |
| 2003/0093101 A1 | 5/2003 | O'Heeron et al. | |
| 2003/0130711 A1 | 7/2003 | Pearson | |
| 2003/0199863 A1 | 10/2003 | Swanson | |
| 2004/0054368 A1 | 3/2004 | Truckai et al. | |
| 2004/0118166 A1 | 6/2004 | Huang et al. | |
| 2004/0172051 A1 | 9/2004 | Ravikumar | |
| 2004/0204720 A1 | 10/2004 | Harrington et al. | |
| 2004/0255958 A1 | 12/2004 | Harrington et al. | |
| 2005/0085880 A1 | 4/2005 | Truckai et al. | |
| 2005/0187561 A1 * | 8/2005 | Lee-Sepsick et al. | 606/108 |
| 2005/0217680 A1 | 10/2005 | Callister et al. | |
| 2005/0273094 A1 * | 12/2005 | Ryan | 606/41 |

FOREIGN PATENT DOCUMENTS

| | | |
|---|---|---|
| DE | 22 22 820 | 11/1973 |
| DE | 4001086 | 1/1990 |
| EP | 0 056 178 A1 | 4/1981 |
| EP | 0 584 930 A1 | 7/1993 |
| EP | 1 400 182 | 6/2004 |
| FR | 774.550 | 9/1934 |
| FR | 70.43012 | 6/1972 |
| JP | 48-67586 | 9/1973 |
| JP | 58-32756 | 2/1983 |
| JP | 63-318934 | 12/1988 |
| WO | WO 92/19145 | 11/1992 |
| WO | WO 94/00178 | 1/1994 |
| WO | WO 94/07445 | 4/1994 |
| WO | WO 94/10948 | 5/1994 |
| WO | WO 94/23794 | 10/1994 |
| WO | WO 95/04385 | 2/1995 |
| WO | WO 95/05869 | 3/1995 |
| WO | WO 95/07664 | 3/1995 |
| WO | WO 95/10326 | 4/1995 |
| WO | WO 99/58070 | 11/1999 |
| WO | WO 01/97897 | 12/2001 |

OTHER PUBLICATIONS

C. Nibley et al., "Prevention of Impedance Rise During Radiofrequency Current Catheter Ablation by Intra-Electrode Tip Chilling," *Circulation* [Abstracts From the 67th Scientific Sessions, Dallas Convention Center, Dallas, Texas, Nov. 14-17, 1994], vol. 90, No. 4, Part 2, Oct. 1994, p. 460.

W.M. Jackman et al., "Radiofrequency Current Directed Across the Mitral Anulus With a Bipolar Epicardial-Endocardial Catheter Electrode Configuration in Dogs," *Circulation*, vol. 78, No. 5, Nov. 1988, pp. 1288-1298.

"Essure: the non-incisional approach to permanent birth control", Patient Information Booklet, © 2004 by Conceptus Incorporated.

"Tubal Ligation—Fimbriectomy: Tubal Reversal is Possible after Fimbriectomy" Datasheet [on-line] Chapel Hill Tubal Reversal Center, 2004 [retrieved on Oct. 19, 2004] Retrieved from the Internet: <URL: http://www.tubal-reversal.net/print/printer-friendly-tubal_ligation_fimbriectomy.htm >.

"Tubal Ligation and Resection: Tubal Ligation by Parkland and Irving Methods" Datasheet [on-line] Chapel Hill Tubal Reversal Center, 2004 [retrieved on Oct. 19, 2004] Retrieved from the Internet: <URL: http://www.tubal-reversal.net/print/printer-friendly-tubal_ligation_resection.htm >.

"Tubal Ligation—Tubal Ring or Clip: Tubal Ligation with Tubal Rings or Tubal Clips" Datasheet [on-line] Chapel Hill Tubal Reversal Center, 2004 [retrieved Oct. 19, 2004] Retrieved from the Internet: <URL: http://www.tubal-reversal.net/tubal_ligation-tubal_ring-tubal_clip.htm >.

"Tubal Ligation—Pomeroy Technique: Pomeroy Tubal Ligation and Resection" Datasheet [on-line] Chapel Hill Tubal Reversal Center, 2004 [retrieved Oct. 19, 2004] Retrieved from the Internet: < http://www.tubal-reversal.net/print/printer-friendly-tubal_ligation_Pomeroy.htm >.

"Tubal Ligation Methods: Coagulation Methods of Tubal Ligation" Datasheet [on-line] Chapel Hill Tubal Reversal Center, 2004, [retrieved Oct. 19, 2004] Retrieved from the Internet: < http://www.tubal-reversal.net/tubal_ligation_coagulation.htm >.

"Essure, Permanent Birth by Conceptus: What is Essure?" Product Information Sheet [on-line] [retrieved Oct. 19, 2004] Retrieved from the Internet: < URL: http://www.essure.com/consumer/c_what_is_essure.aspx >.

* cited by examiner

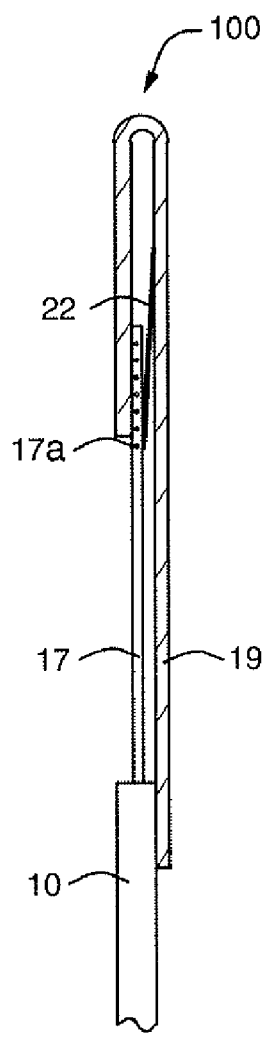
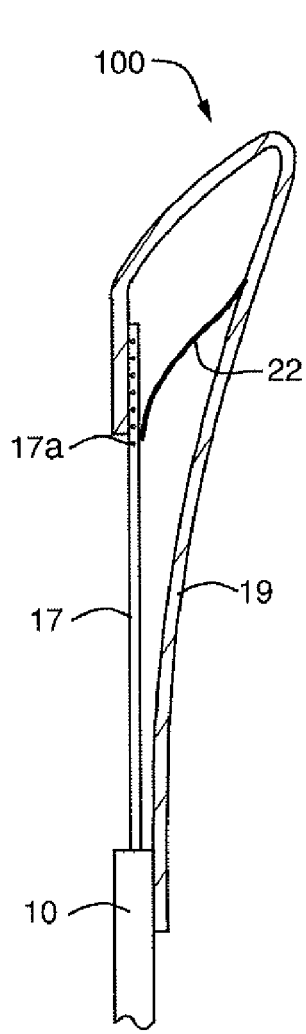
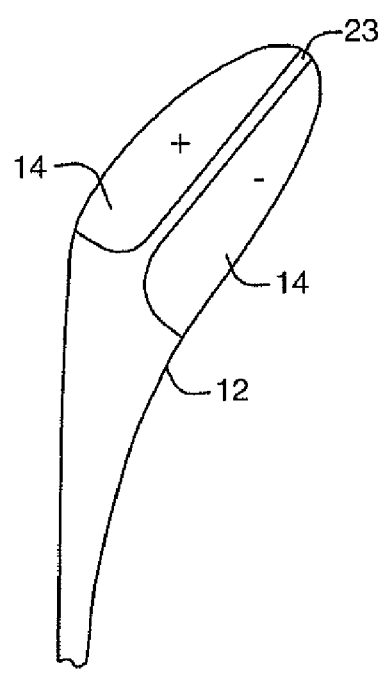
FIG. 4A    FIG. 4B    FIG. 4C
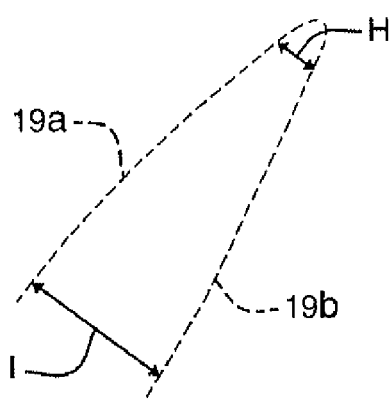
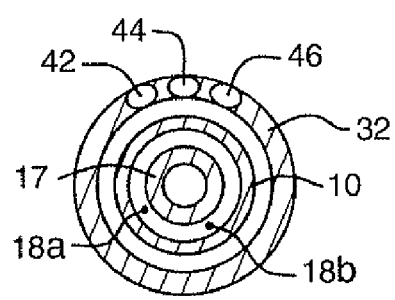
FIG. 4D    FIG. 4E

US 7,731,712 B2

METHOD AND SYSTEM FOR TRANSCERVICAL TUBAL OCCLUSION

TECHNICAL FIELD

This invention relates to a medical device and procedure.

BACKGROUND

Female sterilization typically involves occluding the fallopian tubes to prevent sperm access to an egg within a female's fallopian tube. One conventional female sterilization procedure is laparoscopic tubal occlusion. In this procedure, an incision is made in the abdominal wall to provide access to the fallopian tubes. The tubes are surgically occluded with the aid of a laparoscope, for example, using bipolar or monopolar coagulation. Laparoscopic tubal occlusion is invasive and requires multiple incisions and passing of several instruments and a gaseous distension medium into the patient's abdomen. Thermal and mechanical injury to the surrounding tissues and organs has been reported.

Minimally invasive transcervical approaches to female sterilization have been used more recently. One such procedure involves placing small, flexible devices into the fallopian tubes; the devices are inserted transcervically into the uterine cavity providing access to the fallopian tubes. The devices are made from polyester fibers and metals and once in place, body tissue grows into the devices and blocks the fallopian tubes. The devices permanently remain in the patient's body, which has raised concerns about the long term effects of the implanted devices as well as restrictions on potential subsequent surgical interventions within the uterus, given the conductive metallic components in the devices.

A monopolar radio frequency technique has been investigated that included passing a small diameter wire (an active electrode) transcervically through the uterine cavity and the tubal ostium to the fallopian tubes. A large, passive electrode is positioned externally. The current path between the two electrodes is not well defined and can lead to inadvertent burns. The technique was not successful and was abandoned. It could manage neither the varying thicknesses of endometrial tissue at the tubal ostium, nor the required tight tolerance on the depth of destruction within the fallopian tubes.

SUMMARY

This invention relates to a medical device and procedure. In general, in one aspect, the invention features a method for fallopian tubal occlusion. A tubal occlusion device is inserted into a uterine cavity. The device includes an RF applicator head including an electrode carrier with one or more bipolar electrodes thereon. During insertion, the RF applicator head is in a closed position. The RF applicator head is positioned at a tubal ostium of a fallopian tube such that a distal tip of the RF applicator head advances into the tubal ostium. The RF applicator head is deployed into an open position such that the RF applicator head approximates the shape of the uterine cavity in a region of the tubal ostium. Current is passed through the one or more bipolar electrodes to the tubal ostium to destroy tissue to a known depth, which precipitates a healing response in surrounding tissue that over time scars and occludes the fallopian tube.

Implementations of the invention can include one or more of the following features. Passing current through the one or more bipolar electrodes to the tubal ostium to destroy tissue can include vaporizing endometrium and destroying superficial myometrium. Inserting a tubal occlusion device into a uterine cavity can include inserting the tubal occlusion device with the RF applicator head in a closed position, and before passing current through the one or more bipolar electrodes, deploying the RF applicator head into the open position. Suction can be applied through the electrode carrier to draw the surrounding tissue into contact with the electrodes, and to draw moisture generated during ablation away from the electrodes to substantially prevent the formation of a low impedance liquid layer at the electrodes. Passing current through the one or more bipolar electrodes can include delivering radio frequency energy to the one or more bipolar electrodes.

The method can further include automatically terminating the flow of current into the tissue once ablation has approximately reached a predetermined depth of ablation. Before positioning the RF applicator head at the tubal ostium, the uterine cavity can be insufflated. Insufflation is ceased before passing current through the one or more bipolar electrodes, allowing the uterine cavity to collapse onto the RF applicator head. Deploying the RF applicator head into an open position can include removing a sheath to expose the electrode carrier. The electrode carrier can include a fabric having conductive metallized regions and one or more non-conductive regions formed thereon to create the one or more bipolar electrodes. The method can further include advancing an illuminator and an optical instrument into the uterine cavity. Positioning the RF applicator head at the tubal ostium of a fallopian tube can include using the optical instrument to visualize the tubal ostium.

In general, in another aspect, the invention features a system for fallopian tubal occlusion. The system includes a tubal occlusion device, a source of radio frequency energy, a controller and a vacuum source. The tubal occlusion device has a distal end and a proximal end, the distal end including an electrode carrier with one or more bipolar electrodes thereon. In an open condition the distal end is shaped to approximate a uterine cavity in a region of a tubal ostium of a fallopian tube to be occluded. The source of radio frequency energy is electrically coupled to the one or more bipolar electrodes. The controller is configured to control the delivery of radio frequency energy to the one or more bipolar electrodes such that passing radio frequency energy through the one or more bipolar electrodes to the tubal ostium can be controlled to destroy tissue to a known depth, which precipitates a healing response in surrounding tissue that over time scars and occludes the fallopian tube. The vacuum source is operable to draw the tissue into contact with the one or more bipolar electrodes and to draw moisture generated during delivery of the radio frequency energy to the bipolar electrodes away from the bipolar electrodes. This can substantially eliminate liquid surrounding the bipolar electrodes.

Implementations of the invention can include one or more of the following features. Passing radio frequency energy through the one or more bipolar electrodes to the tubal ostium destroying tissue can include vaporizing endometrium and destroying superficial myometrium. The electrode carrier can include a structural support member within a fabric sheath having conductive metallized regions and having one or more non-conductive regions formed thereon to create the one or more bipolar electrodes. The structural support member can include flexible members movable between a closed condition and the open condition. The system can further include an illumination source electrically coupled to the distal end of the tubal occlusion device to illuminate the uterus, and an optical instrument electrically coupled to the distal end of the tubal occlusion device to provide images of the uterus.

In general, in another aspect, the invention features an apparatus for occluding a fallopian tube. The apparatus includes an elongate member, an electrode carrier and a tube. The elongate member has a distal end, a proximal end and a hollow central interior. The electrode carrier is attached to the distal end of the elongate member and has one or more bipolar electrodes formed thereon. The electrode carrier is operable to couple to a radio frequency energy generator and is movable between a closed position in which the electrode carrier is collapsed for insertion into a uterine cavity, and an open position in which a distal end of the electrode carrier is shaped to fit within a tubal ostium of a fallopian tube. The hollow central interior of the elongate member is operable to couple to a vacuum source and to draw moisture away from the one or more electrodes.

Implementations of the invention can include one or more of the following features. The apparatus can further include an illuminator attached to the distal end of the elongate member and operable to couple to an illumination source, and an optical instrument attached to the distal end of the elongate member and operable couple to an image display device. The electrode carrier can include a structural support member within a fabric sheath having conductive metallized regions and have one or more non-conductive regions formed thereon to create the one or more bipolar electrodes The structural support member can include flexible members movable between a closed condition and the open condition.

Implementations of the invention can realize one or more of the following advantages. The tubal occlusion procedure described is minimally invasive: the tubal occlusion device can be introduced into the patient's uterine cavity transcervically and requires no abdominal incision. The procedure does not leave any foreign objects in the patient's body, minimizing the risk of infection and eliminating the need to restrict subsequent surgical intervention options. The procedure can be performed quickly, the actual duration of ablation being approximately one minute per fallopian tube. Because the RF energy is limited to the region of ablation, there is less risk of damage to other organs during the procedure. The system and procedure automatically compensate for varying endometrial thicknesses, facilitating the proper, contoured depth of tissue destruction in the region of the tubal opening. Further, unlike the technique described above that implanted permanent devices in the fallopian tubes, there is no need to navigate a catheter through the fallopian tubes, which are prone to spasm, inhibiting the placement of permanent devices, making such a procedure difficult to achieve.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A and 4B show one embodiment of a structural body of a RF applicator head in closed and open positions respectively.

FIG. 4C is a schematic representation of a RF applicator head in an open position.

FIG. 4D is a schematic representation of center lines of electrodes of the RF applicator head of FIG. 4C.

FIG. 4E is a cross-sectional view of a main body of the tubal occlusion device of FIGS. 2 and 3.

Like reference symbols in the various drawings indicate like elements.

DETAILED DESCRIPTION

Figure 1A:
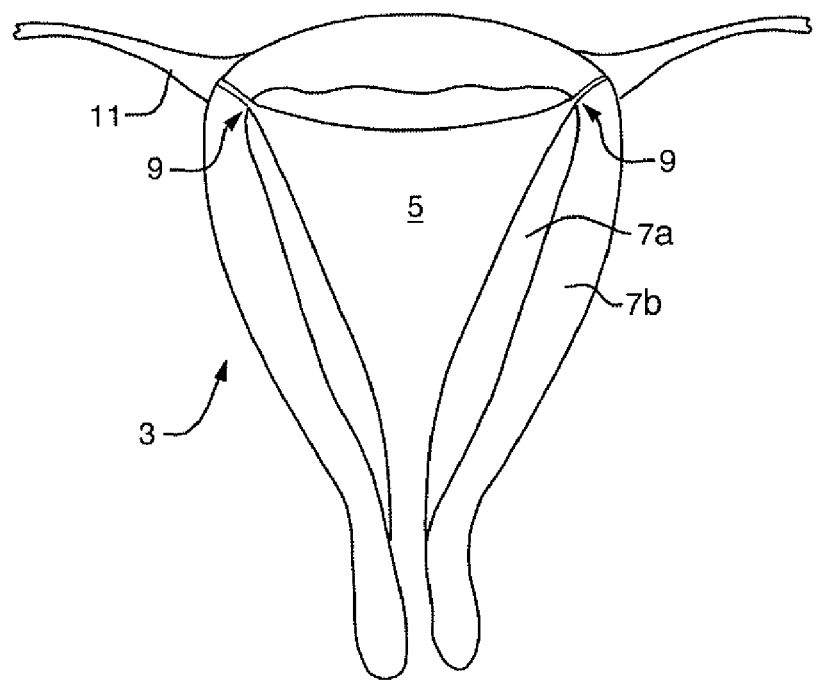
FIG. 1A is a schematic representation of a uterus.

A method and system for occlusion of a female's fallopian tubes is described that provides a minimally invasive alternative for female sterilization. Referring to FIG. 1A, a schematic representation of a uterus 3 is shown, including a uterine cavity 5 surrounded by uterine tissue, namely endometrial tissue 7a and myometrial tissue 7b. The fallopian tubes 11 connect to the uterine cavity 5 at the tubal ostia 9. Occluding the tubal ostia 9 prevents sperm from entering the fallopian tubes 11 and fertilizing an egg, thereby sterilizing the female.

Figure 1B:
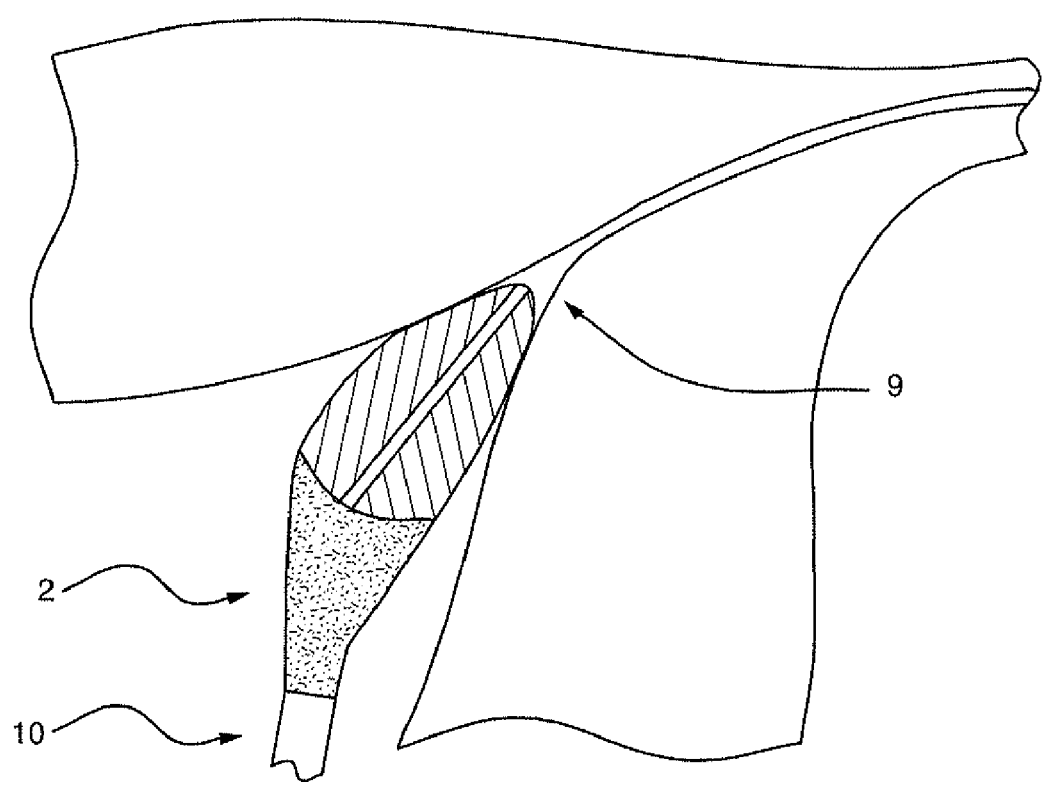
FIG. 1B is a schematic representation of a RF applicator head positioned in a tubal ostium.
Figure 1C:
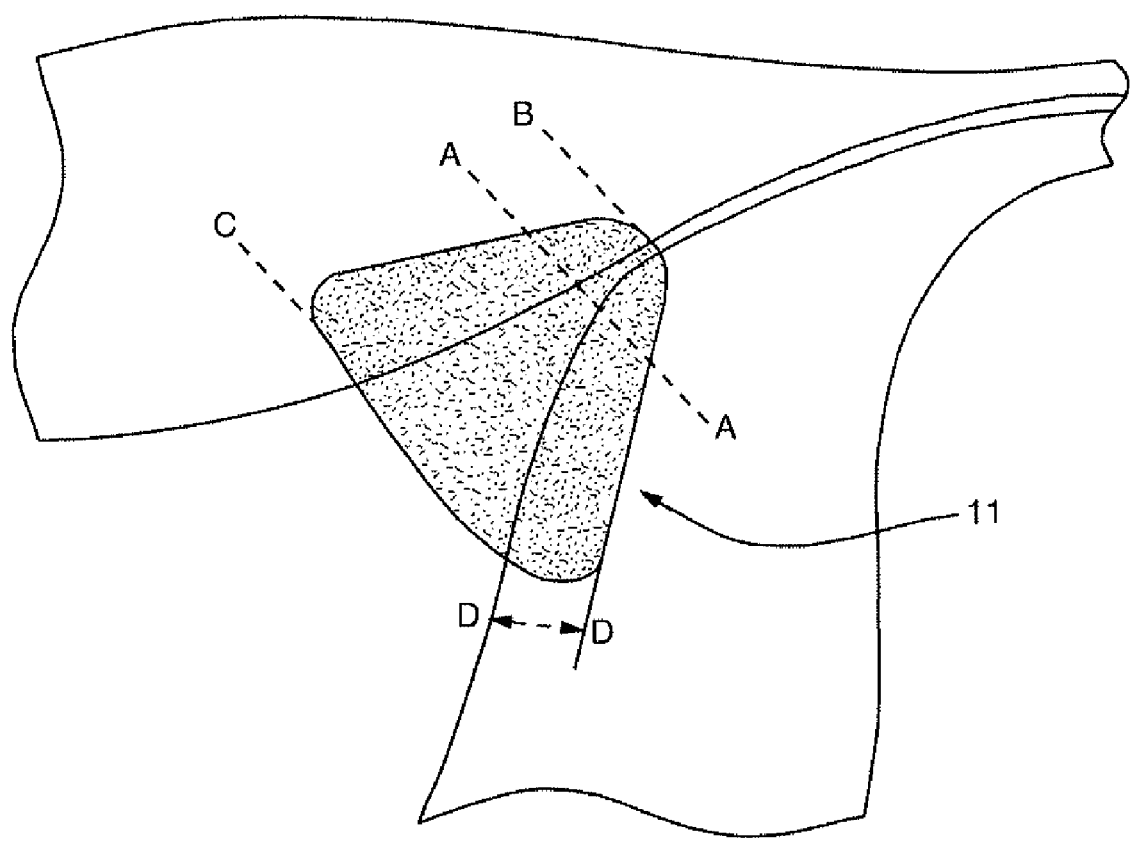
FIG. 1C is a schematic representation of a region of ablated tissue in a uterus and tubal ostium.

Referring to FIG. 1B, a RF (radio frequency) applicator head 2 can be introduced transcervically into the uterine cavity and positioned at a tubal ostium 9. Transmitting RF energy through the RF applicator head 2 ablates the uterine tissue 7a, 7b and tissue within the tubal ostium 9, as shown schematically by the region 11 in FIG. 1C. Following the destruction of tissue at the tubal ostium 9, the healing response occludes the tubal ostium 9 and the adjacent portion of the fallopian tube 11 resulting in sterilization. Referring again to FIG. 1C, the targeted destruction from A-A to B is approximately 1.5 to 2.5 millimeters, from A-A to C is approximately 10 to 20 millimeters, and the depth D-D is typically approximately 2.0 to 3.5 millimeters.

Figure 2:
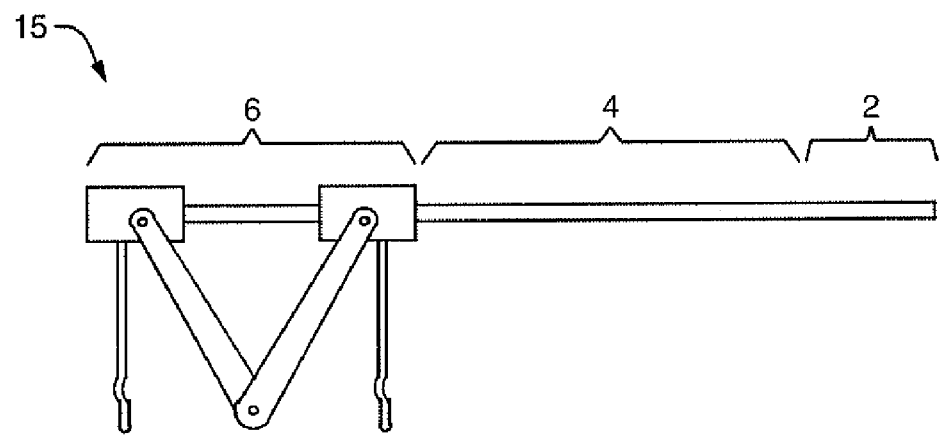
FIG. 2 shows a side view of a tubal occlusion device.
Figure 3A:
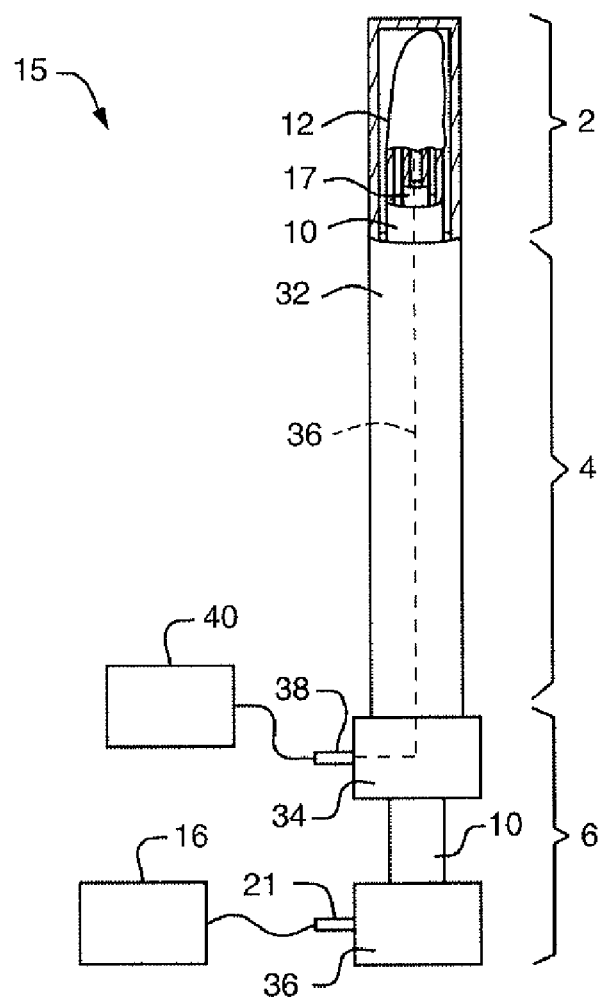
FIG. 3A shows a top view of the tubal occlusion device of FIG. 2 with a RF applicator head in a closed position.
Figure 3B:
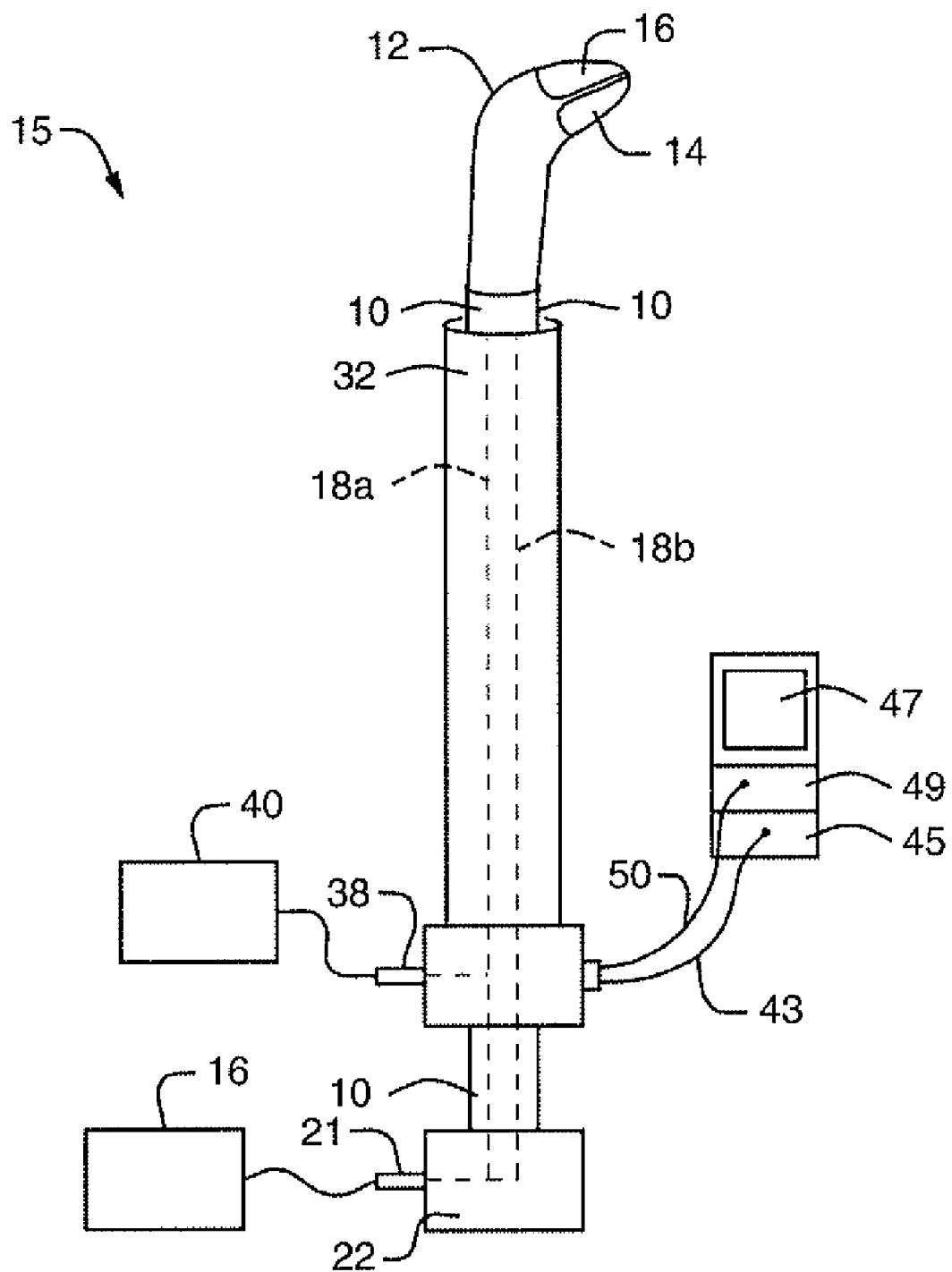
FIG. 3B shows a top view of the tubal occlusion device of FIG. 2 with the RF applicator head in an open position.

Referring to FIGS. 2, 3A and 3B, one embodiment of a tubal occlusion device 15 is shown. The tubal occlusion device 15 includes generally three major components: the RF applicator head 2, a main body 4, and a handle 6. FIG. 2 shows a side view of the tubal occlusion device 15 and FIGS. 3A and 3B show top views. FIG. 3A shows the tubal occlusion device 15 with the RF applicator head 2 in a closed position within a sheath 32 and FIG. 3B shows the RF applicator head 2 in an open position outside of the sheath 32. The RF applicator head 2 includes an electrode carrier 12 mounted to the distal end of the shaft 10 and electrodes 14 formed on the surface of the electrode carrier 12. An RF generator 16 can be electrically connected to the electrodes 14 to provide mono-polar or bipolar RF energy to them.

The main body 4 includes a shaft 10. The shaft 10 is an elongate member having a hollow interior. In one embodiment, the shaft 10 is approximately 30 centimeters long and has a cross-sectional diameter of approximately 4 millimeters. Extending through the shaft 10 is a suction/insufflation tube 17 having a plurality of holes 17a formed in its distal end (see FIGS. 4A and 4B).

Referring particularly to FIG. 3B, electrode leads 18a and 18b extend through the shaft 10 from the distal end 20 to the proximal end 22 of the shaft 10. At the distal end 20 of the shaft 10, each of the leads 18a, 18b is coupled to a respective one of the electrodes 14. At the proximal end 22 of the shaft 10, the leads 18a, 18b are electrically connected to the RF generator 16 by an electrical connector 21. During use, the leads 18a, 18b carry RF energy from the RF generator 16 to the electrodes 14. Each of the leads 18a, 18b is insulated, and the leads 18a and 18b can be connected to opposite terminals of the RF generator 16. When opposite polarity is applied to alternating electrodes or groups of electrodes, an electrode pair (i.e., one positively charged and one negatively charged electrode or group of electrodes) can be referred to as a bipolar electrode. Any references herein to a bipolar electrode refer to such an electrode pair.

Referring to FIGS. 4A-C, the RF applicator head 2 can be shaped to approximate the shape of the region to be ablated. The embodiment of the RF applicator head 2 shown in FIG. 4C has a V-shape which can fit within a corner of the uterine cavity 5 and reach into the tubal ostium 9. FIGS. 4A and 4B show the RF applicator head 2 without the electrode carrier 12, thereby revealing the structural body 100 of the RF applicator head 2. A flexible member 19 is attached to the distal end of the shaft 10 of the main body and to the distal end of the tube 17. A flexure 22 is attached to the tube 17 and to an inner surface of the flexible member 19. In the closed position shown in FIG. 4A, the flexure 22 is compressed within the space formed between the inner surface of the flexible member 19 and the tube 17, and the shape of the structural body 100 of the RF applicator head 2 is substantially cylindrical. In one embodiment, the flexure 22 and flexible member 19 are made from stainless steel, are approximately 0.012 inches thick and are substantially planar.

The RF applicator head 2 can be deployed into the open position shown in FIG. 4B by moving the tube 17 relative to the shaft 10. In one embodiment, the shaft 10 is pulled toward the proximal end of the shaft, i.e., away from the RF applicator head 2. Movement of the shaft 10, which is connected to the flexible member 19, causes the flexible member 19 to also move in the same direction, causing the flexure 22 to move laterally away from the tube 17. As shown in FIG. 4B, flexible member 19 is deformed outwardly, away from the tube 17, creating the V-shape at the distal end of the RF applicator head 2. The shape of the distal end differs depending on how much the shaft 10 and tube 17 are moved relative to one another.

In an alternative embodiment, the tube 17 can be pushed toward the proximal end of the flexible member 19, i.e., toward the RF applicator head 2, thereby moving the tube 17 relative to the shaft 10. The relative movement has the same effect as described above, that is, the flexible member 19 is deformed outwardly, creating a V-shape at the distal end.

FIG. 4C shows the distal end of the RF applicator head 2 with the electrode carrier 12 over the structural body. The electrode carrier 12 can be formed of a fabric that is stretched over the structural body; the fabric is metallized in the regions forming the electrodes 14. The electrodes 14 are conductive and can alternate between positive and negative polarity (an electrode pair being a "bipolar electrode" as described above). In the embodiment depicted, there are four electrodes 14 (or 2 bipolar electrodes), two on either face of the electrode carrier 12. A non-conductive insulator 23 divides the electrode carrier 12 into the bipolar electrodes 14.

In one embodiment, the fabric is formed from a composite yarn with a thermoplastic elastomer (TPE) core and multiple polyfilament nylon bundles wound around the TPE as a cover. The nylon bundles are plated with thin conductive metal layers. Preferably, the nylon is metallized, but not the TPE core. This construction facilitates stretching; the nylon windings open up their coils as the TPE core is elongated, without cracking the metallic layer. The TPE core facilitates recovery from the stretched position, pulling the nylon coils back into their initial configuration.

In an alternative embodiment, the electrode carrier 12 can be a sack formed of a material that is non-conductive, that is permeable to moisture, and that can be compressed to a smaller volume and subsequently released to its natural size upon elimination of compression. Examples of materials for the electrode carrier 12 include foam, cotton, fabric, or cotton-like material, or any other material having the desired characteristics. The electrodes 14 can be attached to the outer surface of the electrode carrier 12, e.g., by deposition or another attachment mechanism. The electrodes 14 can be made of lengths of silver, gold, platinum, or any other conductive material. The electrodes 14 can be formed on the electrode carrier 12 by electron beam deposition, or they can be formed into coiled wires and bonded to the electrode carrier 12 using a flexible adhesive. Other means of attaching the electrodes, such as sewing them onto the surface of the electrode carrier 12, may alternatively be used.

Depth of destruction of the target tissue can be contoured to achieve repeatable, predetermined depths. Variables such as the electrode construction, power applied to the electrodes (power density or power per unit surface area of the electrode), and the tissue impedance at which power is terminated can be used to affect the depth of tissue destruction, as discussed further below.

The spacing between the electrodes (i.e., the distance between the centers of adjacent electrodes) and the widths of the electrodes are selected so that ablation will reach predetermined depths within the tissue, particularly when maximum power is delivered through the electrodes. Maximum power is the level at which low impedance, low voltage ablation can be achieved. For example, referring to FIG. 4D, lines 19a and 19b represent center lines of the electrodes 14 of the RF applicator head 2 of FIG. 4C, i.e., the spacing. The center lines diverge and are closest at the distal end I and further apart at the proximal end H. The closer the center lines the shallower the depth of destruction. That is, the depth of destruction at the distal end, which during operation is positioned within or closest to the tubal ostium 9, is least.

Figure 5A:
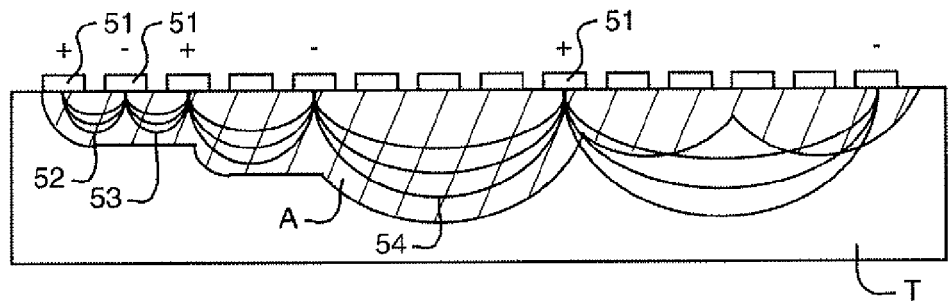
FIGS. 5A-D are schematic representations of cross-sectional views showing electrodes in contact with tissue for ablation.

Referring to FIG. 5A, preferably each electrode is energized at a polarity opposite from that of its neighboring electrodes. By doing so, energy field patterns, designated 52, 53 and 54 in FIG. 5A, are generated between the electrode sites and thus help to direct the flow of current through the tissue T to form a region of ablation A. As can be seen in FIG. 5A, if electrode spacing is increased by energizing, for example, every third or fifth electrode rather than all electrodes, the energy patterns will extend more deeply into the tissue. See, for example, pattern 53 which results from energization of electrodes having a non-energized electrode between them, or pattern 54 which results from energization of electrodes having two non-energized electrodes between them.

The depth of ablation is also effected by the electrode density (i.e., the percentage of the target tissue area which is in contact with active electrode surfaces) and may be regulated by pre-selecting the amount of this active electrode coverage. For example, the depth of ablation is much greater when the active electrode surface covers more than 10% of the target tissue than it is when the active electrode surfaces covers only 1% of the target tissue.

By way of illustration, by using 3-6 mm spacing and an electrode width of approximately 0.5-2.5 mm, delivery of approximately 20-40 watts over a 9-16 $cm^2$ target tissue area will cause ablation to a depth of approximately 5-7 millimeters when the active electrode surface covers more than 10% of the target tissue area. After reaching this ablation depth, the impedance of the tissue will become so great that ablation will self-terminate. By contrast, using the same power, spacing, electrode width, and RF frequency will produce an ablation depth of only 2-3 mm when the active electrode surfaces covers less than 1% of the target tissue area. This can be better understood with reference to FIG. 5B, in which high surface density electrodes are designated 51a and low surface density electrodes are designated 51b. For purposes of this comparison between low and high surface density electrodes, each bracketed group of low density electrodes is considered to be a single electrode. Thus, the electrode widths W and spacings S extend as shown in FIG. 5B.

Figure 5B:
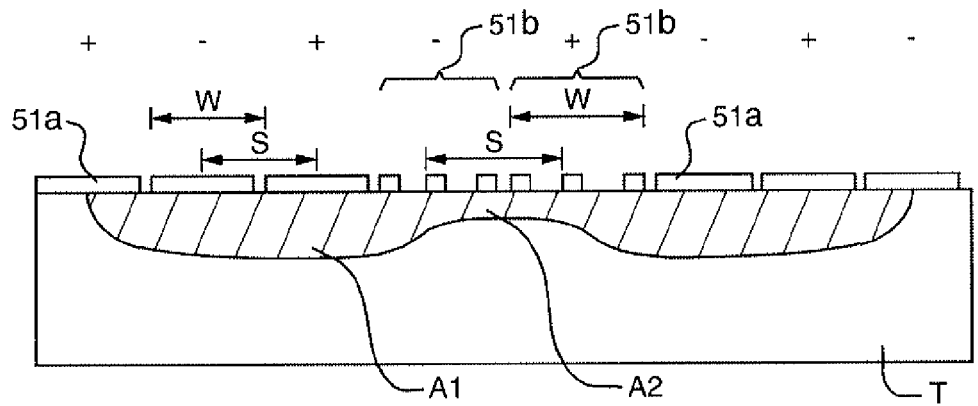

As is apparent from FIG. 5B, the electrodes 51a, which have more active area in contact with the underlying tissue T, produce a region of ablation A1 that extends more deeply into the tissue T than the ablation region A2 produced by the low density electrodes 51b, even though the electrode spacings and widths are the same for the high and low density electrodes. Some examples of electrode widths, having spacings with more than 10% active electrode surface coverage, and their resultant ablation depth, based on an ablation area of 6 cm$^2$ and a power of 20-40 watts, are given on the following table:

| ELECTRODE WIDTH | SPACING | APPROX. DEPTH |
|---|---|---|
| 1 mm | 1-2 mm | 1-3 mm |
| 1-2.5 mm | 3-6 mm | 5-7 mm |
| 1-4.5 mm | 8-10 mm | 8-10 mm |

Examples of electrode widths, having spacings with less than 1% active electrode surface coverage, and their resultant ablation depth, based on an ablation area of 6 cm$^2$ and a power of 20-40 watts, are given on the following table:

| ELECTRODE WIDTH | SPACING | APPROX. DEPTH |
|---|---|---|
| 1 mm | 1-2 mm | 0.5-1 mm |
| 1-2.5 mm | 3-6 mm | 2-3 mm |
| 1-4.5 mm | 8-10 mm | 2-3 mm |

Thus it can be seen that the depth of ablation is significantly less when the active electrode surface coverage is decreased.

Figure 5C:
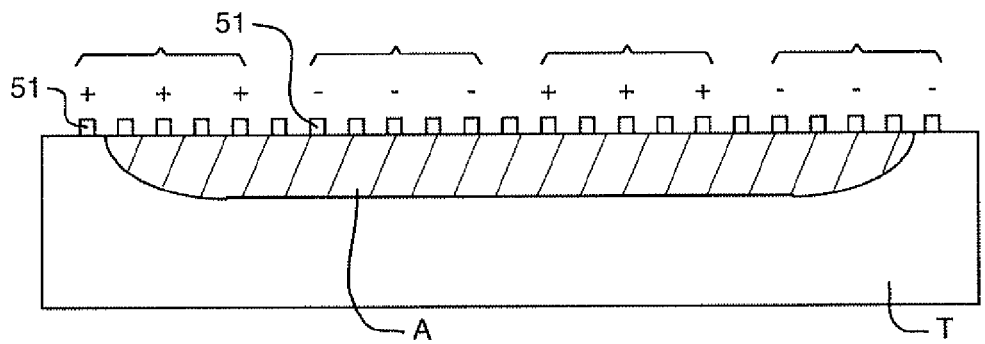
Figure 5D:
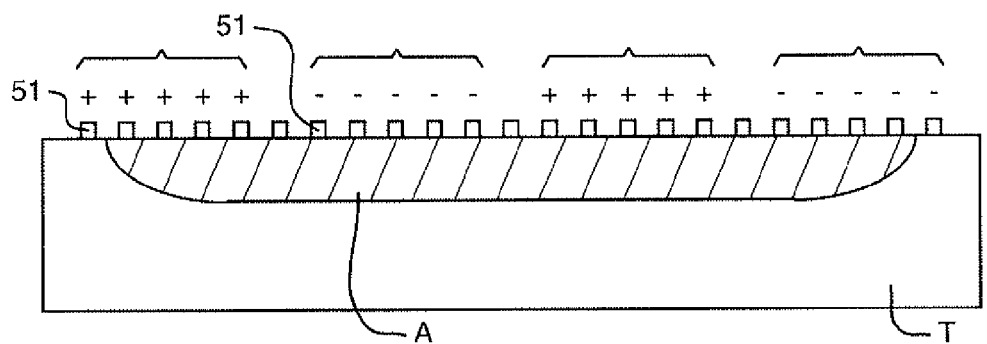
Figure 6:
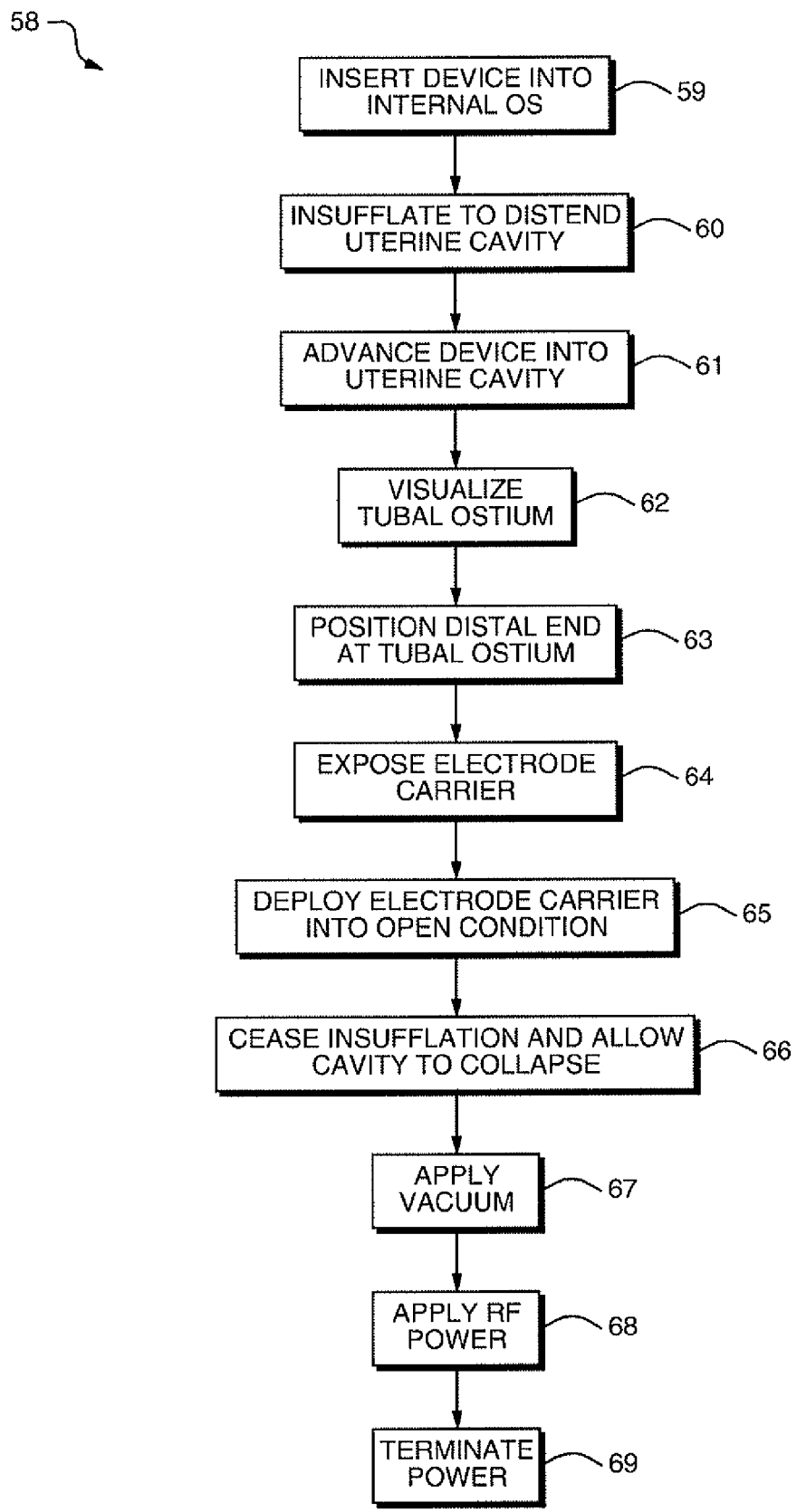
FIG. 6 is a flowchart showing a process for tubal occlusion.

Referring to FIG. 5C, if multiple, closely spaced, electrodes 51 are provided on the electrode carrying member, a user may set the RF generator 16 to energize electrodes which will produce a desired electrode spacing and active electrode area. For example, alternate electrodes may be energized as shown in FIG. 5C, with the first three energized electrodes having positive polarity, the second three having negative polarity, etc. All six electrodes together can be referred to as one bipolar electrode. As another example, shown in FIG. 5D, if greater ablation depth is desired the first five electrodes may be positively energized, and the seventh through eleventh electrodes negatively energized, with the sixth electrode remaining inactivated to provide adequate electrode spacing. Therefore, in one implementation, a user can control which electrodes are energized to produce a desired depth of destruction.

Referring again to FIGS. 3A and 3B, in one implementation, to achieve the desired depth of ablation, a controller included in the RF generator 16 can monitor the impedance of the tissue at the distal end of the RF applicator head 2 and include an automatic shut-off once a threshold impedance is detected. As the tissue is desiccated by the RF energy, fluid is lost and withdrawn from the region by a vacuum through the tube 17, which can be connected to suction/insufflation unit 40 via suction/insufflation port 38 (FIGS. 3A, 3B). The suction draws moisture released by tissue undergoing ablation away from the electrode carrier 12 and prevents formation of a low-impedance liquid layer around the electrodes 14 during ablation. As more tissue is desiccated, the higher the impedance experienced at the electrodes 14. By calibrating the RF generator 16, taking into account system impedance (e.g., inductance in cabling etc.), a threshold impedance level can be set that corresponds to a desired depth of ablation.

Once the threshold impedance is detected, the controller shuts off the RF energy, preventing excess destruction of tissue. For example, when transmitting RF energy of 5.5 watts per square centimeter of tissue, an impedance of the tissue of 50 ohms can indicate a depth of destruction of approximately 3 to 4 millimeters at the proximal end H and approximately 2.5 millimeters at the distal end I. In an alternative embodiment, the RF generator 16 can be configured such that above the threshold impedance level the RF generator's ability to deliver RF power is greatly reduced, which in effect automatically terminates energy delivery.

Referring again to FIGS. 3A and 3B, an introducer sheath 32 facilitates insertion of the tubal occlusion device 15 into, and removal of the device from, the uterine cavity 5. The sheath 32 is a tubular member that is slidable over the shaft 10. The sheath 32 is slidable between a distal condition, shown in FIG. 3A, in which the RF applicator head 2 is compressed inside the sheath, and a proximal condition in which the sheath 32 is moved proximally to release the RF applicator head 2 from inside the sheath 32 (FIG. 3). By compressing the electrode carrier 12 to a small volume, the RF applicator head 2 can be easily inserted transcervically into the uterine cavity 5.

During use, the sheath 32 is retracted from the electrode carrier 12, for example, by moving the distal handle member 34 towards the proximal handle member 37 to slide the sheath 32 in the distal direction. Moving the distal handle member 34 toward the proximal handle member 27 can also advance the shaft 10 in the proximal direction. The movement of the shaft 10 relative to the suction/insufflation tube 17 causes the shaft 10 to pull proximally on the flexible member 19. Proximal movement of the flexible member 19 in turn pulls the flexure 22, causing it to move to the opened condition shown in FIG. 3B (see also FIG. 4B). In one embodiment, a locking mechanism (not shown) is required to hold the shaft in the fully withdrawn condition to prevent inadvertent closure of the RF applicator head 2 during the ablation procedure.

The amount by which the flexible member 19 is deformed outwardly from the tube 17 can be controlled by manipulating the handle 6 to slide the shaft 10, proximally or distally. The amount by which the shaft 10 is slid relative to the tube 17 controls the shape of the flexible member 19.

As mentioned above, in an alternative embodiment, the handle 6 can be configured so that the tube 17 can be moved distally relative to the shaft 10. Distal movement of the tube 17 in turn deforms the flexible member 19 outwardly. The amount by which the flexible member 19 is deformed outwardly from the tube 17 can be controlled by manipulating the handle 6 to slide the tube 17 proximally or distally, and the amount by which the tube 17 moves relative to the shaft 10 controls the shape of the flexible member 19.

As shown in FIG. 3A, a flow pathway 36 is formed from the RF applicator head 2 to the suction/insufflation port 38. The proximal end of the suction/insufflation tube 17 is fluidly coupled to the flow pathway so that gas fluid may be introduced into, or withdrawn from the suction/insufflation tube 17 via the suction/insufflation port 38. For example, suction may be applied to the fluid port 38 using a suction/insufflation unit 40. This causes water vapor within the uterine cavity 5 to pass through the permeable electrode carrier 12, into the suction/insufflation tube 17 via holes 17a, through the tube 17, and through the suction/insufflation unit 40 via the port 38. If insufflation of the uterine cavity 5 is desired, insufflation gas, such as carbon dioxide, may be introduced into the suction/insufflation tube 17 via the port 38. The insufflation gas travels through the tube 17, through the holes 17a, and into the uterine cavity 5 through the permeable electrode carrying member 12.

One or more additional components can be provided for endoscopic visualization purposes. For example, lumen 42, 44, and 46 may be formed in the walls of the introducer sheath 32 as shown in FIG. 4E. An optical instrument can be used to provide images from within the uterine cavity. For example, referring to FIGS. 3B and 4E, an imaging conduit, such as a fiberoptic bundle, extends through lumen 42 and is coupled via a camera cable 43 to a camera 45. Images taken from the camera may be displayed on a monitor 47. An illumination fiber 50 can extend through lumen 44 and couple to an illumination source 49. The optional third lumen 46 can be an instrument channel through which surgical instruments may be introduced into the uterine cavity 5, if necessary. In an alternative embodiment, one or more of the lumen 42, 44, 46 can be formed in the walls of the shaft 10.

Because during use it is most desirable for the electrodes 14 on the surface of the electrode carrier 12 to be held in contact with the interior surface of the uterine cavity 5 and tubal ostia 9, the electrode carrier 12 may have additional components inside it that add structural integrity to the electrode carrying means when it is deployed within the body.

Referring to FIGS. 1A-C, 5 and 6A-D, a process 58 for using the tubal occlusion device 15 to sterilize a female shall be described. The tubal occlusion device 15 is inserted through the vagina and cervix to the internal os 13 at the base of the uterus 3 (step 59). A gas, e.g., carbon dioxide, is delivered into the uterine cavity 5 via the suction/insufflation tube 17 from the suction/insufflation unit 40 to distend the uterine cavity 5 (step 60). The tubal occlusion device 15 is then advanced into the uterine cavity 5 (step 61).

Figure 7A:
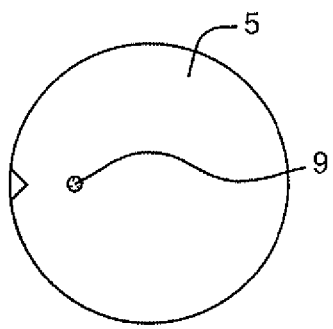
FIGS. 7A-D are schematic representations of steps of a process for tubal occlusion.
Figure 7B:
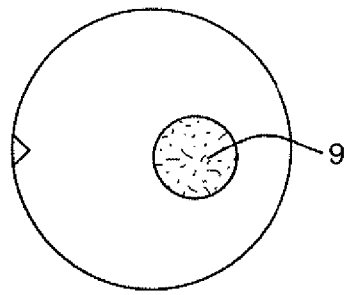
Figure 7C:
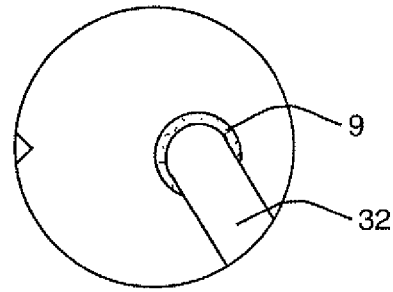
Figure 7D:
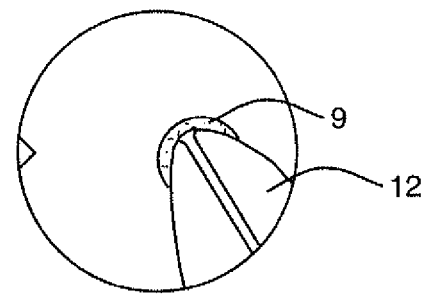

The user visualizes the target tubal ostium 9 on the monitor 47 using images provided by the camera 45 (step 62). FIG. 7A is a schematic representation of what the user may see upon the tubal occlusion device 15 entering the uterine cavity 5; the tubal ostium 9 is a relatively small spot in the distance. As the tubal occlusion device 15 advances toward the tubal ostium 9, the tubal ostium 9 is easier to visualize, as shown in FIG. 7B. The distal end of the RF applicator head 2, which is still within the sheath 32, is positioned at the tubal ostium 9, as depicted in FIG. 7C (step 63). The sheath 32 is withdrawn to expose the electrodes 14 (step 64) and the RF applicator head 2 is deployed into the open position (step 65), as depicted in FIG. 7D.

Insufflation is ceased and the uterine cavity 5 is allowed to collapse onto the RF applicator head 2 (step 66). Vacuum can be applied to the RF applicator head 2 via the suction/insufflation tube 17 to draw the surrounding tissue into contact with the electrodes 14 (step 67). The RF generator 16 is turned on to provide RF energy to the electrodes 14 (step 68). The RF energy is ceased once the desired amount of tissue has been ablated (step 69). In one implementation, 5.5 watts of RF power is supplied for per square centimeter of electrode surface area until the predetermined impedance threshold is reached, at which point power is terminated.

The uterine cavity 5 can be insufflated a second time, the RF applicator head 2 collapsed into a closed position and the tubal occlusion device 15 rotated approximately 180°. The RF applicator head 2 can then be positioned at the other tubal ostium 9 and the above procedure repeated to ablate tissue at the other tubal ostium 9. The tubal occlusion device 15 is then closed and withdrawn from the patient's body. After ablation, healing and scarring responses of the tissue at the tubal ostia 9 permanently occlude the fallopian tubes 11, without requiring any foreign objects to remain in the female's body and without any incisions into the female's abdomen. The procedure is fast, minimally invasive, and is highly effective at tubal occlusion.

Figure 8:
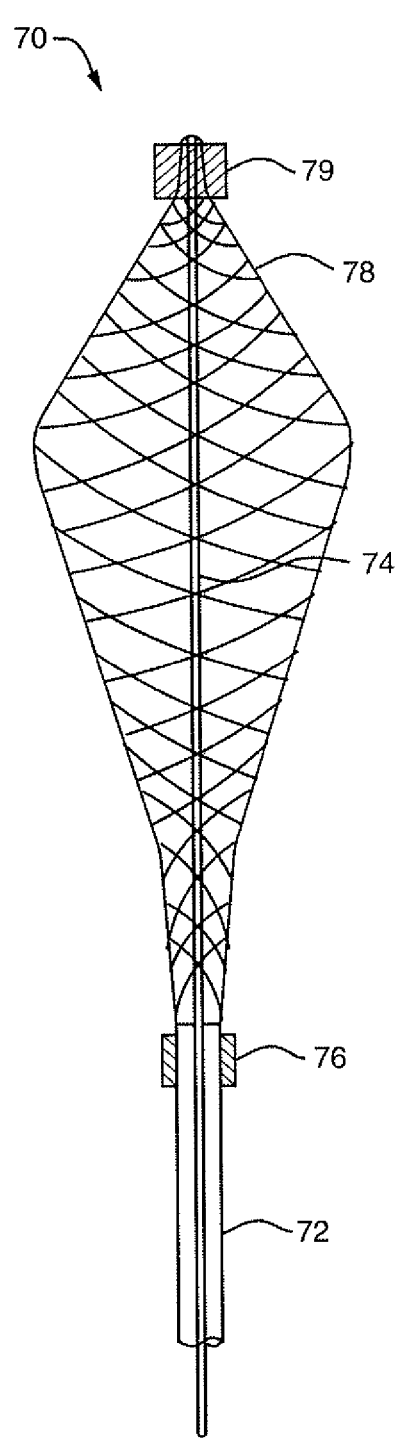
FIG. 8 is a schematic representation of an alternative embodiment of a structural body of a RF applicator head.

Referring to FIG. 8, an alternative embodiment of a structural body 70 of the RF applicator head 2 is shown. The structural body 70 includes an external hypotube 72 and an internal hypotube 74. If implementing the structural body 70 in the embodiment of the tubal occlusion device 15 described above, the external hypotube 72 can be the shaft 10 and the internal hypotube 74 can be the suction/insufflation tube 17. A cage 78 is formed over the internal hypotube 74 configured in a V-shape at the distal end 79 that can reach into a tubal ostium 9. The cage 78 can be a braided or woven structure made from a memory material, e.g., nitinol.

The cage 78 can be collapsed into a narrow cylindrical configuration by moving the internal hypotube 74 relative to the external hypotube 72, e.g., by pushing the internal hypotube 74 distally away from the external hypotube 72. In a collapsed state the cage 78 can fit, for example, within the sheath 32 described above, when the RF applicator head 2 is placed in a closed position. Once the sheath 32 is removed and the internal hypotube 74 is moved back into the open position relative to the external hypotube 72, the nature of the material from which the cage 78 is made expands the cage 78 into the desired shape that is depicted. An electrode carrier, such as the electrode carrier 12 made from a metallized fabric described above, can be fitted over the structural body 70, completing the RF applicator head.

A number of embodiments of the invention have been described. Nevertheless, it will be understood that various modifications may be made without departing from the spirit and scope of the invention. Accordingly, other embodiments are within the scope of the following claims.

What is claimed is:

1. A system for fallopian tubal occlusion, comprising:
   a tubal occlusion device having a distal end and a proximal end, the distal end including an electrode carrier with two faces, each face having two bipolar electrodes thereon, said electrode carrier comprising a structural support member within a fabric sheath having conductive metallized regions and having one or more non-conductive regions formed thereon to create the bipolar electrodes, and is shaped to approximate a uterine cavity in a region of a tubal ostium of a fallopian tube to be occluded, wherein the bipolar electrodes are arranged on the carrier to target tissue destruction over a length of 10 mm to 20 mm along an endometrium from the tubal ostium;
   a source of radio frequency energy electrically coupled to the bipolar electrodes;
   a controller configured to control the delivery of radio frequency energy to the bipolar electrodes such that passing radio frequency energy through the bipolar electrodes to the tubal ostium can be controlled to destroy tissue to a known depth that precipitates a healing response in surrounding tissue that over time scars and occludes the fallopian tube; and a vacuum source operable to draw the tissue into contact with the bipolar electrodes and to draw moisture generated during delivery of the radio frequency energy to the bipolar electrodes away from the bipolar electrodes and to substantially eliminate liquid surrounding the bipolar electrodes.

2. The system of claim 1, wherein the bipolar electrodes are adapted to deliver radiofrequency energy to the tubal ostium under conditions which vaporize the endometrium and destroy superficial myometrium.

3. The system of claim 1, wherein the structural support member includes flexible members movable between a closed condition and the open condition.

4. The system of claim 1, further comprising:

an illumination source electrically coupled to the distal end of the tubal occlusion device to illuminate the uterus; and an optical instrument electrically coupled to the distal end of the tubal occlusion device to provide images of the uterus.

5. An apparatus for occluding a fallopian tube of a patient having two fallopian tubes comprising:

an elongate member having a distal end, a proximal end and a hollow central interior; and an electrode carrier attached to the distal end of the elongate member and including two faces, each face having two bipolar electrodes formed thereon and operable to couple to a radio frequency energy generator, said electrode further including a structural support member within a fabric sheath having conductive metallized regions and having one or more non-conductive regions formed thereon to create the bipolar electrodes, the electrode carrier is movable between a closed position in which the electrode carrier is collapsed for insertion into a uterine cavity and an open position in which a distal end of the electrode carrier is shaped to fit within a tubal ostium of a single fallopian tube without entering into a tubal ostium of the second fallopian tube, and the hollow central interior of the elongate member is operable to couple to a vacuum source and to draw moisture away from the bipolar electrodes.

6. The apparatus of claim 5, further comprising:

an illuminator attached to the distal end of the elongate member and operable to couple to an illumination source; and an optical instrument attached to the distal end of the elongate member and operable couple to an image display device.

7. The apparatus of claim 5, wherein the structural support member includes flexible members movable between a closed condition and the open condition.

8. An apparatus as in claim 5, wherein the bipolar electrodes on the electrode carrier are arranged to target treatment to endometrial tissue extending along a length from 10 mm to 20 mm from the tubal ostium.

* * * * *